US011033397B2

(12) United States Patent
Jang et al.

(10) Patent No.: US 11,033,397 B2
(45) Date of Patent: Jun. 15, 2021

(54) ARTIFICIAL KNEE JOINT

(71) Applicant: CORENTEC CO. LTD., Cheonan-si (KR)

(72) Inventors: Young-Woong Jang, Seoul (KR); Chan-Eol Kim, Seoul (KR); Jae-Hun Ro, Seoul (KR); Ah-Reum Han, Gangwon-do (KR); Myung-Chul Lee, Gyeonggi-do (KR); Yong In, Seoul (KR); Seung-Beon Han, Seoul (KR)

(73) Assignee: Corentec Co. Ltd., Chungcheonghan-do (KR)

( * ) Notice: Subject to any disclaimer, the term of this patent is extended or adjusted under 35 U.S.C. 154(b) by 116 days.

(21) Appl. No.: 16/233,497

(22) Filed: Dec. 27, 2018

(65) Prior Publication Data

US 2020/0046506 A1 Feb. 13, 2020

(30) Foreign Application Priority Data

Aug. 8, 2018 (KR) ........................ 10-2018-0092372

(51) Int. Cl.

| | |
|---|---|
| ***A61F 2/38*** | (2006.01) |
| *A61F 2/30* | (2006.01) |
| *A61F 2/46* | (2006.01) |

(52) U.S. Cl.

CPC ............ *A61F 2/385* (2013.01); *A61F 2/3877* (2013.01); *A61F 2/389* (2013.01); *A61F 2/461* (2013.01); *A61F 2002/30001* (2013.01)

(58) Field of Classification Search

CPC ........ A61F 2/385; A61F 2/389; A61F 2/3886; A61F 2/461

See application file for complete search history.

(56) References Cited

U.S. PATENT DOCUMENTS 8,764,840 B2 * 7/2014 Sanford ................ A61F 2/3836 623/20.32
9,480,569 B2 * 11/2016 Roisin ..................... A61F 2/389

FOREIGN PATENT DOCUMENTS

KR 10-1352066 A 1/2014

* cited by examiner

*Primary Examiner* — Brian A Dukert
(74) *Attorney, Agent, or Firm* — Workman Nydegger

(57) ABSTRACT

An artificial knee joint includes a tibial component implanted into the proximal end of a tibia, and a bearing component coupled to the tibial component, in which the tibial component includes an interference prevention portion capable of preventing interference with the bearing component when the bearing component is inserted diagonally and the bearing component includes a protrusion coupled to the interference prevention portion.

4 Claims, 12 Drawing Sheets

5 P 53 551 535 L 3323 3 332 M A

9

ARTIFICIAL KNEE JOINT

CROSS-REFERENCE TO RELATED APPLICATIONS

This application claims priority to Korean Application No. 10-2018-0092372, filed Aug. 8, 2018, the entire contents of which is incorporated herein by specific reference.

BACKGROUND OF THE INVENTION

1. Field of the Invention

The present disclosure relates to an artificial knee joint, and more particularly, to an artificial knee joint including a tibial component implanted into the proximal end of a tibia, and a bearing component coupled to the tibial component, in which the tibial component includes an interference prevention portion capable of preventing interference with the bearing component when the bearing component is inserted diagonally, and the bearing component includes a protrusion coupled to the interference prevention portion.

2. Description of the Prior Art

Among numerous joints of a body, the knee joint is a joint that connects the tibia and the femur, and the number of patients who have irrecoverable knee joint damage due to wear of knee joints, aging of bone tissues, and accidents have been gradually increasing. The knee joint is a joint located between the lower end of the femur, the upper end of the tibia, and the rear surface of the patella (knee bone), and functions to flex the leg backward from the knee.

Recently, replacement of a knee with an artificial knee joint has been widely performed in patients who have irrecoverable knee joint damage due to serious injury. For the joint motion portion of the artificial knee joint, metal, ceramic, polyethylene, or the like is used to improve the mechanical property, lower the friction coefficient, and enhance the biocompatibility. In general, an artificial knee joint is divided into a femur insertion member coupled to the tip of the femur, a tibial component coupled to the tip of the tibia, and a bearing component (corresponding to the cartilage) located between the femur insertion element and the tibial component. Here, the femur insertion member and the tibial component are mainly made of a metal alloy, and the bearing component is made of polyethylene or the like.

FIG. 1 is a perspective view of an artificial knee joint according to the prior art, and FIG. 2 is an exploded perspective view of FIG. 1. The artificial knee joint is disclosed in Korean Patent No. 10-1352066. Referring to FIGS. 1 and 2, an artificial knee joint 9 includes a bearing component 95 coupled to the upper side of a tibial component 93 to replace the cartilage of the actual knee joint, and a tibial component 93 inserted into the upper side of the tibia and coupled with the bearing component 95 by receiving the bearing component 95 at the upper side thereof.

The bearing component 95 includes an upper portion 951 that provides a joint surface that is in contact with a femoral component (not shown) and performs joint motion, and a lower portion 952 that extends downwards from the bottom surface of the upper portion through a step so as to be coupled with the tibial component 93.

In addition, the tibial component 93 includes a base plate 933 that defines a coupling space into which the lower portion of the bearing component is inserted, and a stem 931 extending from the lower side of the base plate.

The base plate 933 includes a plate bottom 9331 and a rim 9332 extending upwards along the lateral peripheral edge of the plate bottom.

The base plate 933 of the tibial component 93 and the lower portion 953 of the bearing component 95 have corresponding shapes and structures so as to be mutually coupled. Such a configuration is disclosed in Korean Patent No. 10-1352066.

In the process of applying the artificial knee joint 9, when the bearing component 95 is coupled to the tibial component 93, it is important to align the bearing component 95 with the tibial component 93 so as to be coupled at a prescribed position. This is because when the coupling is not performed at a prescribed position, the bearing component 95 may be damaged, or the tibial component 93 may be dislocated.

A minimally invasive knee joint replacement operation in which a skin incision portion is minimized is desirable for a patient. The minimally invasive knee joint replacement operation minimizes incision and dissection of the skin and soft tissue for a surgical operation, and is advantageous in that in addition to fewer cosmetic problems, there are less bleeding during the surgical operation and less pain after the surgical operation, and the recovery period is short and the rehabilitation treatment is fast because ligaments are not cut. However, in the process of a minimally invasive knee joint replacement operation, various restrictions are imposed on the surgical operation. For example, since the tibial component 93 is inserted and then the tibial component 93 is finally coupled with the bearing component 95 in the state where the incision is made in medial direction and the patella is pushed aside in the lateral direction, a restriction is caused in that the bearing component 95 should be inserted in an oblique direction due to surrounding tissues.

FIG. 3 is a view showing the state of use of the artificial knee joint according to the prior art, in which a bearing component is inserted into a tibial component in an oblique direction, and FIG. 4 is a view showing the state in which interference occurs while the bearing component is inserted into the tibial component in the oblique direction to be coupled to the tibial component following the state in FIG. 3. FIG. 5A is a view obtained by projecting the tibial component onto the plane from the upper side, FIG. 5B is a view obtained by projecting the bearing component onto the plane from the upper side, and FIG. 5C is a view obtained by projecting the bearing component and the tibial component onto the plane from the upper side, in the state in which the bearing component is inserted into the tibial element in the oblique direction.

As illustrated in FIG. 3, when a surgical operation is performed in an oblique direction, a surgeon moves the bearing component 95 in the oblique direction toward the tibial component 93 implanted into the proximal end of the tibia, and then, positions the left or right rear end 953*a* of the lower portion 953 of the bearing component 95 in the medial space of the rim 9332 of the base plate 933 corresponding thereto, i.e., in the left or right space of the space. As illustrated in FIGS. 5A to 5C, the length of the line segment a-a' in the major axis, which is the longest axis in the medial coupling space of the rim 9332 of the base plate 933, and the length of the line segment b-b' in the major axis, which is the longest axis in the lower portion of the insert are substantially equal to each other. Thus, when the bearing component 95 is inserted in the oblique direction with respect to the tibial component 93, the major axis line segment b-b' of the lower portion of the bearing component 95 is located at a position deviated from the major axis line segment a-a' of the base plate. Consequently, as illustrated in FIG. 3, a part of the lower portion 953 of the bearing component 95 collides with the upper end of the rim 9332 of the base plate 933, and as illustrated in FIG. 4, the left or right rear side 953*a* of the lower portion 953 of the bearing component 95, which has already been inserted, is raised upwards, which makes insertion in the oblique direction difficult. Referring to FIG. 5C, since the major axis line segment b-b' of the lower portion of the bearing component is longer than the line segment c-c' obtained by interconnecting the points where the major axis of the lower portion of the insert intersects the inner end on the top surface of the rim of the base plate, the insertion in the oblique direction becomes difficult.

SUMMARY OF THE INVENTION

The present disclosure has been conceived in order to solve the problems described above.

An aspect of the present disclosure is to provide an artificial knee joint, in which an interference prevention portion is provided so as to prevent interference between the bearing component and the tibial component when the bearing component is inserted in an oblique direction, whereby the insertion in the oblique direction can be facilitated.

Another aspect of the present disclosure is to provide an artificial knee joint, in which a protrusion, having a shape complementary to the shape of the interference prevention portion and coupled to the interference prevention portion, is provided, so that the coupling position between the tibial component and the bearing component can be easily aligned.

Still another aspect of the present disclosure is to provide an artificial knee joint, in which the protrusions of the bearing component and the invagination recesses in the tibial component are coupled to each other with the complementary shapes thereof, whereby the rotation of the bearing component by the movement of the artificial knee joint can be prevented and the position of the bearing component can be maintained.

Yet another aspect of the present disclosure is to provide an artificial knee joint, in which coupling is made without a gap between the protrusions and invagination recesses, so that in the process of recovery after surgical operation has been terminated, it is possible to prevent side effects such as the surrounding tissues being caught in a coupling gap in the recovery process after the operation process is terminated.

In view of the above aspects of the present disclosure, the present disclosure is implemented by embodiments having configurations as follows.

According to an embodiment of the present disclosure, an artificial knee joint includes a tibial component implanted into a proximal end of a tibia, and a bearing component coupled to the tibial component. The tibial component includes an interference prevention portion configured to prevent interference of the tibial component with the bearing component during insertion thereof in an oblique direction with respect to the bearing component.

According to another embodiment of the present disclosure, the tibial component includes a base plate coupled to the bearing component, and the interference prevention portions are provided in the base plate.

According to another embodiment of the present disclosure, the interference prevention portions are provided in the lateral peripheral edge of the tibial component.

According to another embodiment of the present disclosure, the interference prevention portions are invagination recesses provided at predetermined positions in the lateral peripheral edge of the tibial component.

According to another embodiment of the present disclosure, the base plate includes a rim protruding along the lateral peripheral edge thereof, and the invagination recesses are provided in the rim.

According to another embodiment of the present disclosure, the interference prevention portions are provided symmetrically with reference to an A-P line.

According to another embodiment of the present disclosure, the interference prevention portion(s) includes one end and a remaining end, and with reference to an M-L line, the one end is located at a posterior side and the remaining end is located at an anterior side.

According to still another embodiment of the present disclosure, the bearing component includes a protrusion coupled to the interference prevention portion.

According to still another embodiment of the present disclosure, the protrusion has a shape complementary to a shape of the interference prevention portion.

The present disclosure is capable of obtaining the following effects through a combination and use relationship of the above-described embodiment and the configurations to be described below.

According to the present disclosure, an interference prevention portion is provided so as to prevent interference between the bearing component and the tibial component when the bearing component is inserted in an oblique direction, whereby the insertion in the oblique direction can be facilitated.

According to the present disclosure, the protrusions, having a shape complementary to the shape of the interference prevention portions and coupled to the interference prevention portions, are provided, so that the coupling position between the tibial component and the bearing component can be easily aligned.

According to the present disclosure, the protrusions of the bearing component and the invagination recesses in the tibial component are coupled to each other with the complementary shapes thereof, whereby the rotation of the bearing component, which is caused by the movement of the artificial knee joint, can be prevented and the position of the bearing component can be maintained.

According to the present disclosure, since coupling is made without a gap between the protrusions and invagination recesses, it is possible to prevent side effects such as the surrounding tissues being caught in a coupling gap in the recovery process after the operation process is terminated.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Figure 1:
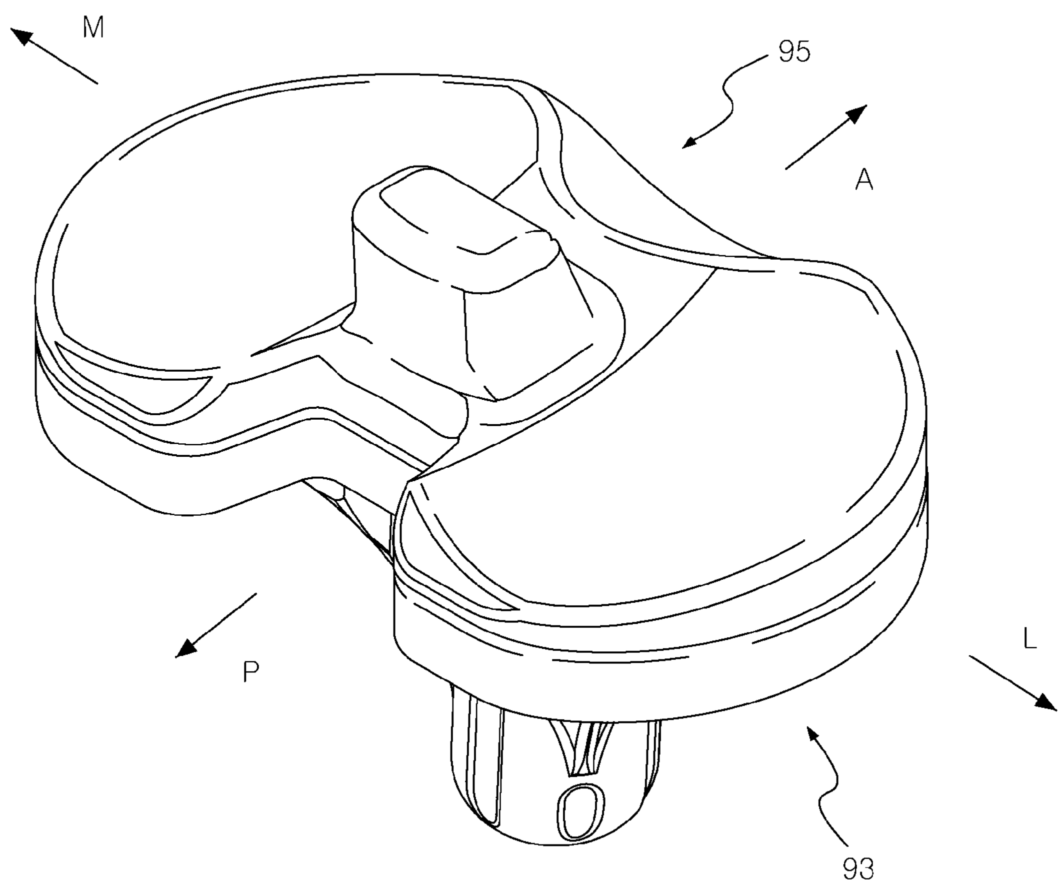
FIG. 1 is a perspective view of an artificial knee joint according to the prior art.
Figure 2:
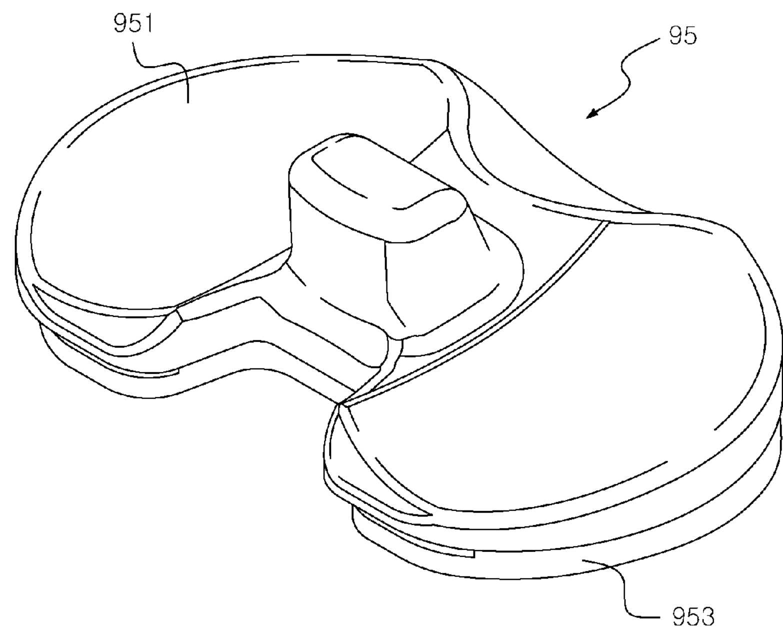
FIG. 2 is an exploded perspective view of FIG. 1.
Figure 2:
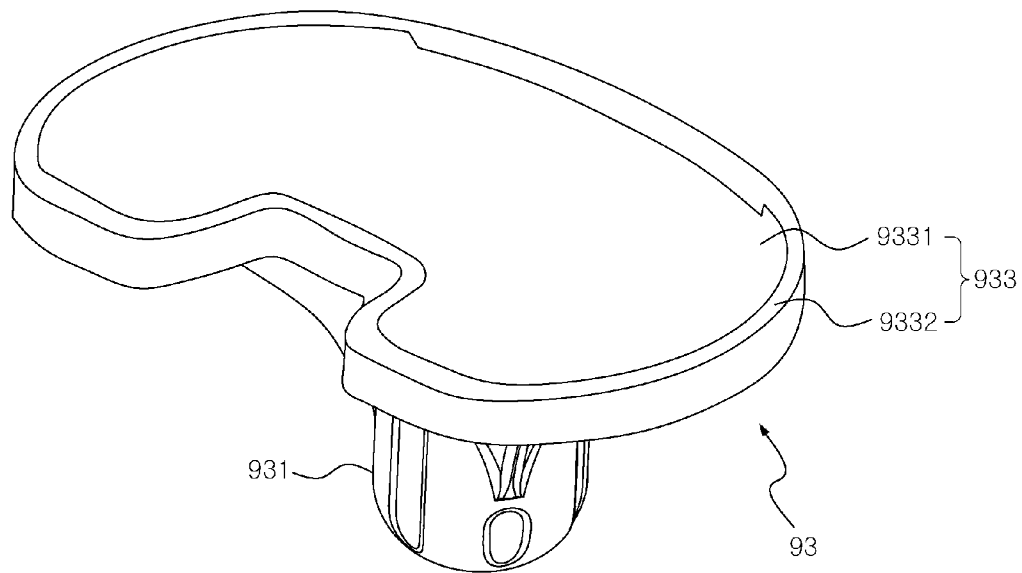
Figure 3:
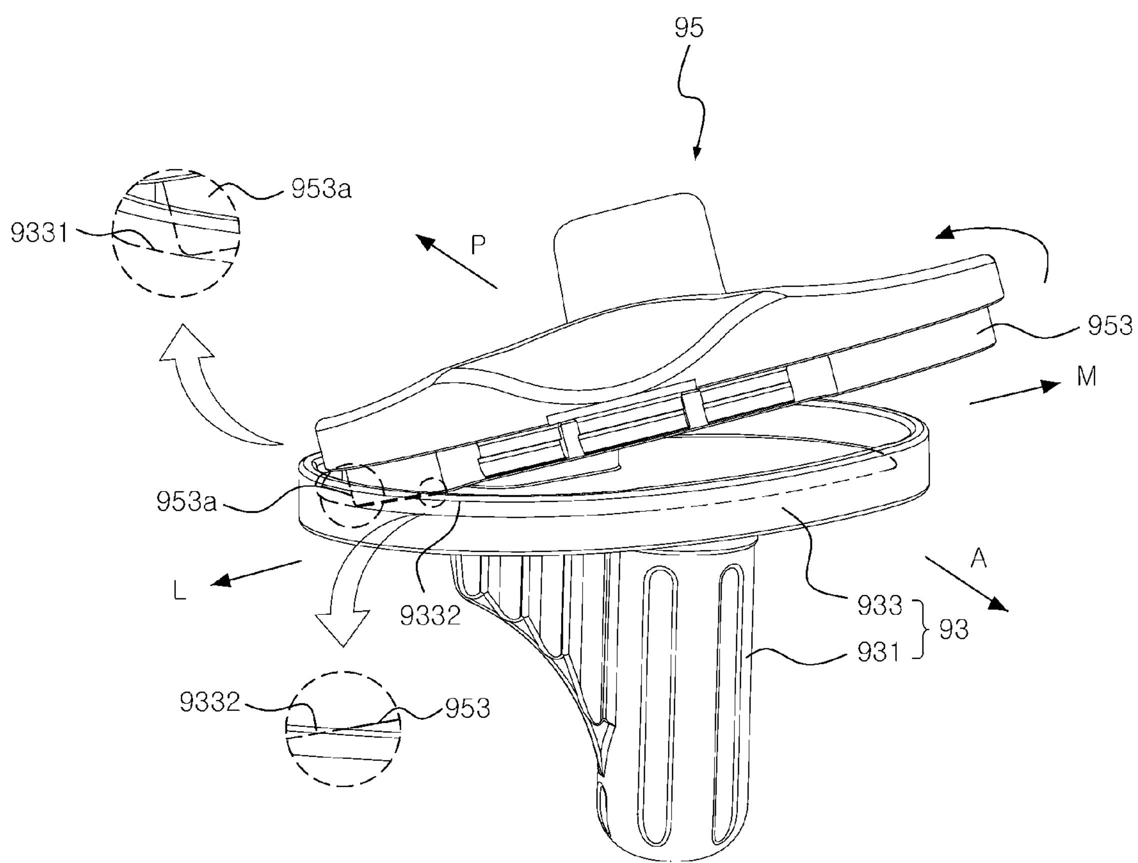
FIG. 3 is a view showing the state of use of the artificial knee joint according to the prior art, in which a bearing component is inserted into a tibial component in an oblique direction.
Figure 4:
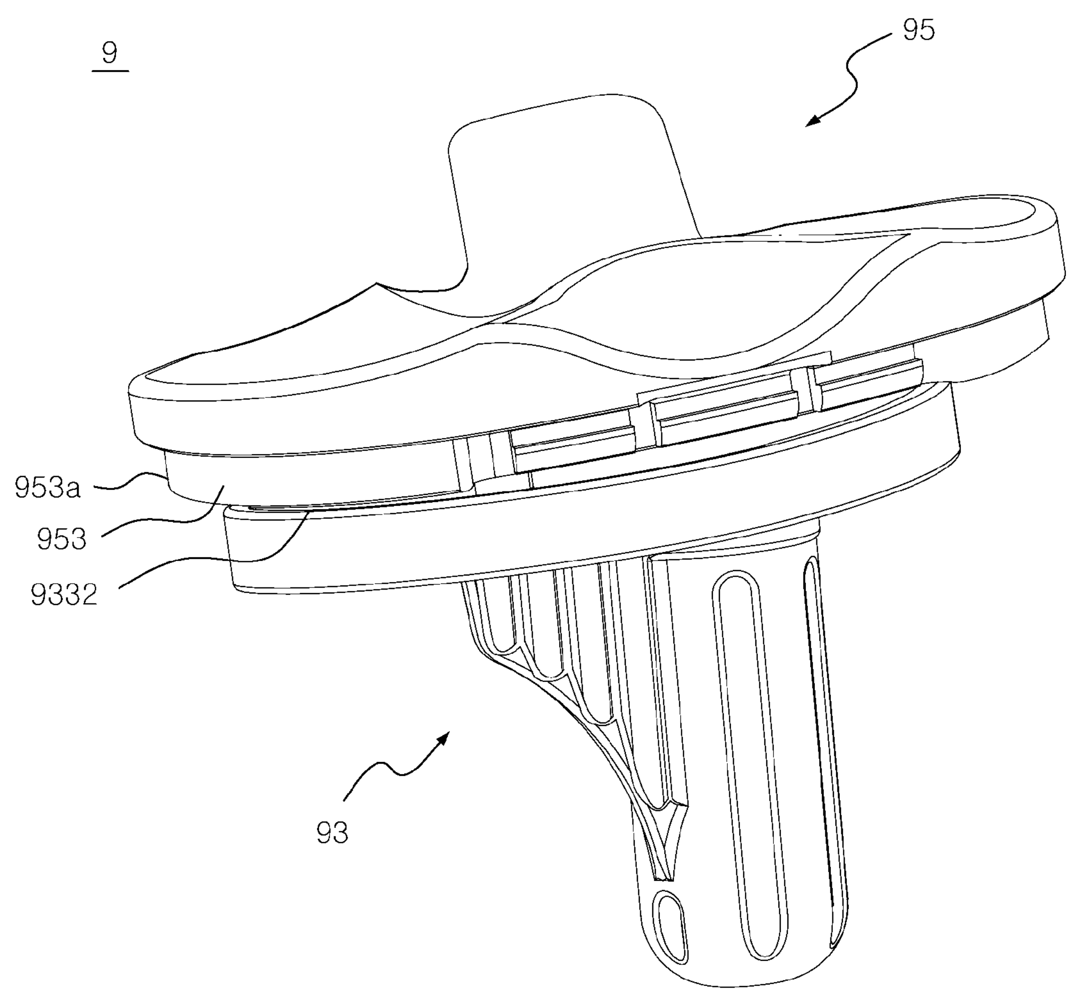
FIG. 4 is a view showing the state in which interference occurs while the bearing component is inserted into the tibial component in an oblique direction to be coupled to the tibial component following the state of FIG. 3.
Figure 5B:
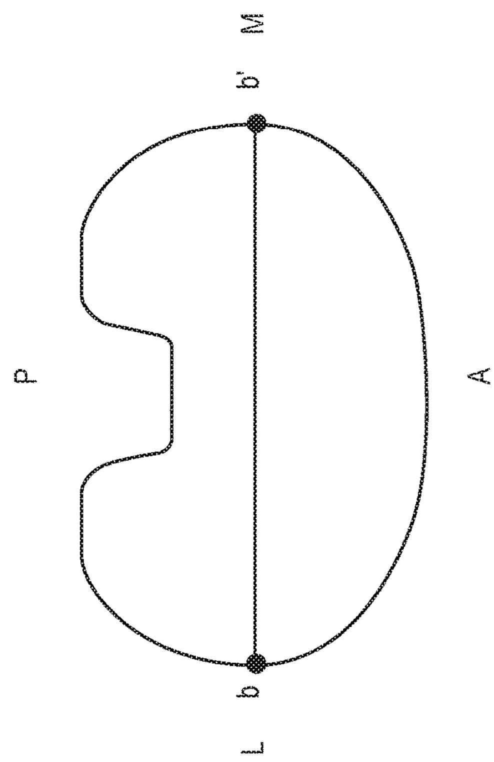
FIG. 5B is a view obtained by projecting the bearing component onto the plane from the upper side.
Figure 5C:
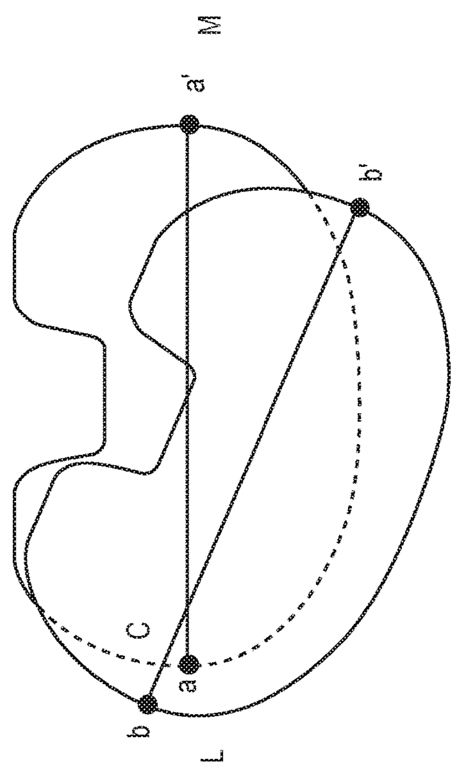
FIG. 5C is a view obtained by projecting the bearing component and the tibial component onto the plane from the upper side, in the state in which the bearing component is inserted into the tibial element in the oblique direction.
Figure 5A:
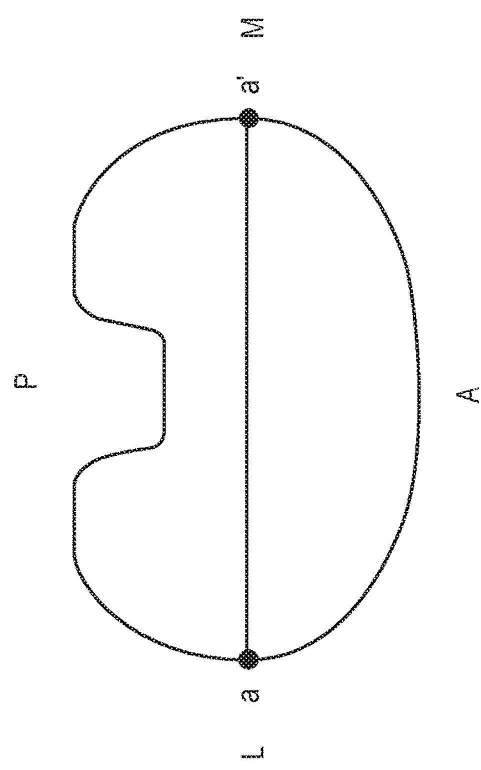
FIG. 5A is a view obtained by projecting the tibial component onto the plane from the upper side.

Hereinafter, an artificial knee joint of the present disclosure will be described in detail with reference to the accompanying drawings. It is to be noted that the same elements among the drawings are denoted by the same reference numerals if possible. In the following description, s detailed description of well-known functions or constructions will be omitted when it may make the subject matter of the present disclosure rather unclear. Unless defined otherwise, all terms used herein have the same meaning as the general meaning of the terms understood by a person ordinarily skilled in the art to which this disclosure belongs and, when the general meaning conflicts with the meaning of the terms used herein, the meaning of the terms follows the definition used in the specification.

In this application, with reference to the coronal plane, "A" indicates the anterior side to which the face of the person is directed and "P" indicates the posterior side to which the rear portion of the head of the person is directed. With reference to the sagital plane, "M" indicates the medial side and "L" indicates the lateral side.

Figure 6:
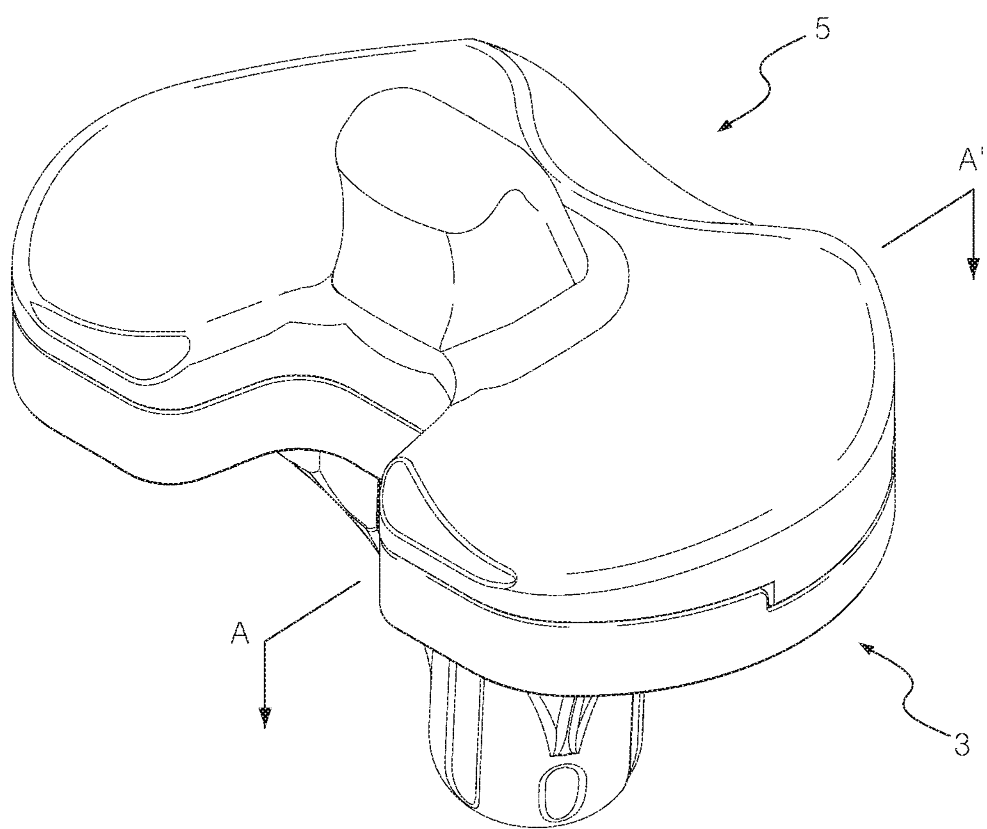
FIG. 6 is a perspective view of an artificial knee joint according to an embodiment of the present disclosure.
Figure 7:
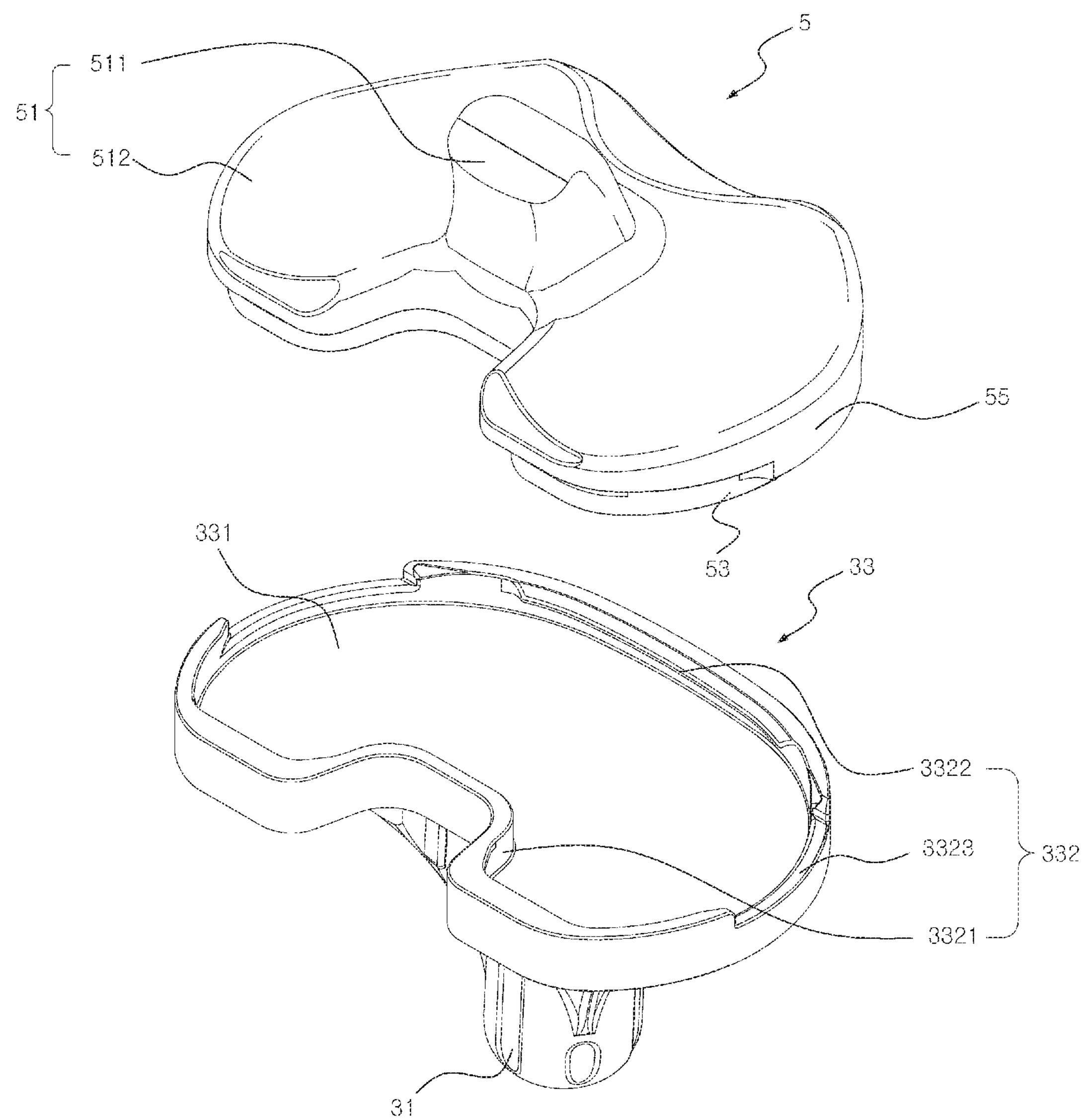
FIG. 7 is an exploded perspective view of FIG. 6.

FIG. 6 is a perspective view of an artificial knee joint according to an embodiment of the present disclosure, and FIG. 7 is an exploded perspective view of FIG. 6. Referring to FIGS. 6 to 7, an artificial knee joint according to an embodiment of the present disclosure includes a tibial component 3 coupled to the tip of a tibia and a bearing component 5 coupled to the upper side of the tibial component, in which a femur insertion member (not shown) is capable of performing joint motion similar to an actual knee joint by performing bending or rotating motion while sliding on the upper surface of the bearing component 5, thereby functioning as an artificial joint.

The tibial component 3 is inserted into the upper side of the tibia and the bearing component 5 is received in the upper side of the tibial component 3 and coupled to the bearing component 5 so as to form a predetermined shape that forms a portion of the tibial component. For this purpose, the tibial component 3 includes a stem 31 and a base plate 33.

The stem 31 is inserted into the patient's tibia in artificial knee joint operation, and may be generally classified into a bone-cement-fixing type for improving the bonding strength between the tibia and the stem 31 and a cementless type in which bond cement is not used. The stem 31 may have other various structures for fixing the stem 31 at the medial side of the tibia.

The base plate 33 is a portion on which the bearing component 5 is seated, and includes a plate bottom 331 and a rim 332. The base plate 33 is generally made of a single metal such as a Ti alloy or a CoCr alloy. When a lamination technique is used, it is possible to make the plate bottom 331 and the rim 332 using different materials.

The rim 332 is erected on the plate bottom 331, and below the plate bottom, there is a bonding surface between the base plate 33 and the stem 331, in which the lower portion of the plate bottom 331 and the upper end surface of the stem are bonded to each other, so that the base plate 33 and the stem 31 are coupled to each other.

The rim 332 protrudes upwards along the lateral peripheral edge of the plate bottom 531 so as to define a coupling space in which the bearing component 5 of the artificial knee joint is seated. The rim 332 may be customized to have different shapes, heights, and sizes depending on the patient, and may include a posterior protrusion 3321, an anterior recess 3322, and invagination recesses 3323.

Figure 10:
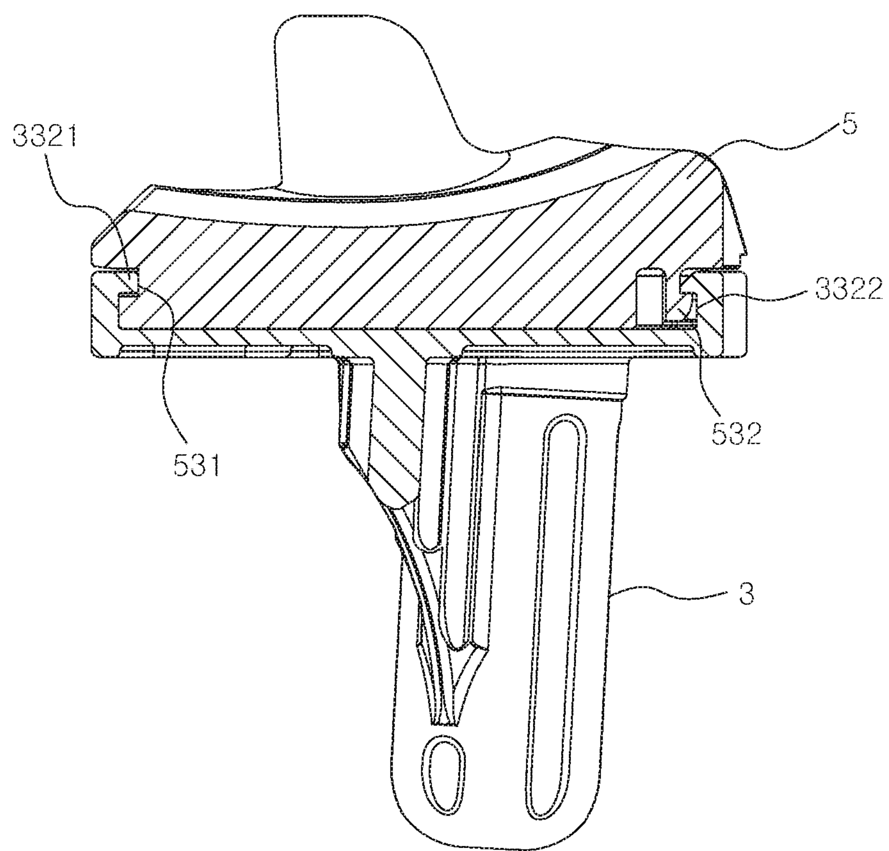
FIG. 10 is a cross-sectional view taken along line A-A' in FIG. 6.

The posterior protrusion 3321 is bent at the rim 332 so as to extend in the horizontal direction, and is inserted into and engaged in a coupling groove 531 in the bearing component 5. Such a coupling relationship is shown in FIG. 10.

The anterior recess 3322 is a portion formed in the process of bending the posterior protrusion 3321 to extend in the horizontal direction, and has a cross section of a letter "⊏" shape. Elastic hooks 532 of the bearing component 5 are inserted into and elastically engaged with the anterior recess 3322. Such a coupling relationship is shown in FIG. 10.

Figure 8:
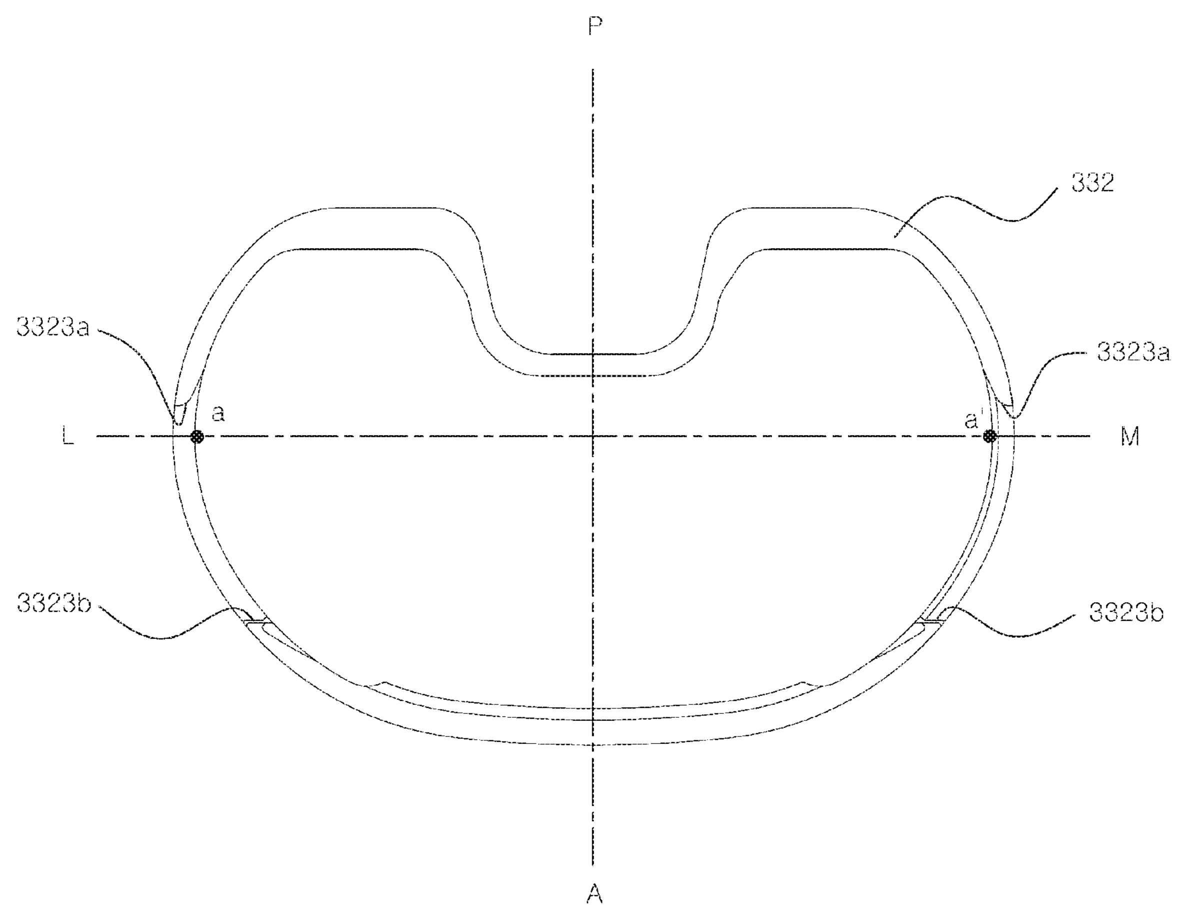
FIG. 8 is a plan view of a tibial component according to the embodiment of the present disclosure.

As shown in FIG. 8, the invagination recesses 3323 are portions invaginated in the rim 332 by a predetermined depth, and has one end **3323*a* at which the invagination is started and a remaining end 3323*b* at which the invagination is terminated. The one end 3323*a* is a portion near the posterior end of the base plate 33, and the remaining end 3323*b* is a portion near the anterior end of the base plate. Here, the posterior end is a portion of the base plate directed toward the posterior side P, and the anterior end is a portion of the base plate directed toward the anterior side A. The interval between the one end 3323*a* and the remaining end 3323*b* and the positions thereof may be variously set, but are set such that in order to insert the bearing component in an oblique direction, when the lateral side L or the medial side M of the lower portion of the inserted insert is positioned in the coupling space of the base plate 33 corresponding to the medial posterior end 535, i.e., the lateral space or medial space of the coupling space, the lower portion of the bearing component positioned at the anterior side of the posterior end thereof does not collide with the medial end of the upper surface of the rim of the base plate. Preferably, with reference to the M-L line, which is the medial-lateral line, the one end 3323*a* is located behind the M-L line, and the remaining end 3323*b*** is located in front of the M-L line.

According to another embodiment of the present disclosure, invagination recesses 3323 are formed in a pair on the medial side M and the lateral side L of the rim of the base plate to be symmetrical to each other. It is not excluded that the intervals or the positions may be formed asymmetrically. For example, the invagination recesses of the medial side M and the invagination recesses of the lateral side L may be formed at different intervals, or the interval of the invagination recesses located in the insertion side may be longer than the interval of the invagination recesses located opposite thereto.

Figure 9:
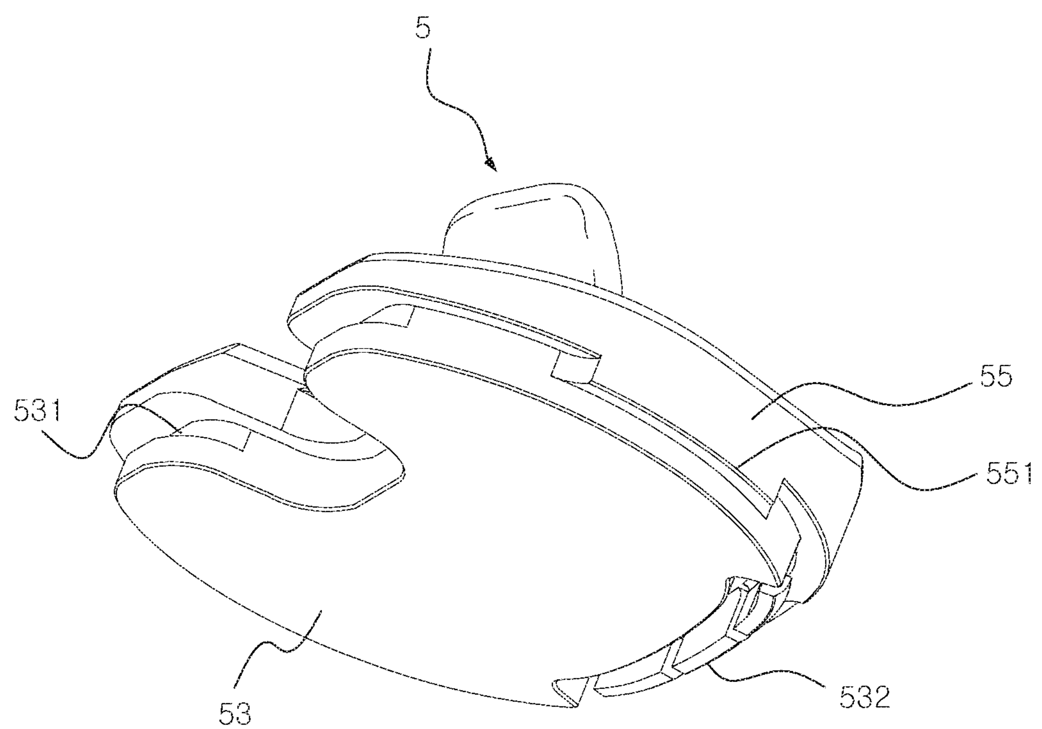
FIG. 9 is a bottom-side perspective view of a bearing component according to the embodiment of the present disclosure.

FIG. 9 is a bottom-side perspective view of a bearing component according to the embodiment of the present disclosure. Referring to FIGS. 7 and 9, the bearing component 5 is disposed between the femur insertion member and the tibial component 3 and replaces the cartilage of the actual knee joint. The bearing component 5 is coupled to the upper side of the tibial component 5, and includes an upper portion 51, a lower portion 55, and a side portion 55.

Referring to FIG. 7, the upper portion 51 includes a post 511 protruding upwards from the bearing component 5, and a groove that extends downwards from the lower end of the post 511 so as to provide a joint surface of the femur insertion member (not shown) and a joint surface, which performs joint motion.

The post 511 protrudes upwards from one side of the upper surface of the bearing component 5. Artificial knee joint operations include a Cruciate-Retaining-type (CR-type) operation and a Posterior-Stabilized-type (PS-type) operation. The CR-type operation is an artificial knee joint operation which is performed in the state in which the posterior cruciate ligament is not removed, and the PS-type operation is an artificial knee joint operation, in which the posterior cruciate ligament is replaced with the post 511 of the bearing component 5 in the state in which the posterior cruciate ligament is removed. In the case of the PS-type artificial knee joint operation, the post 511 of the bearing component 5 and the cam of the femur insertion member replaces the removed posterior cruciate ligament. Accordingly, the post 511 is a structure necessary for the artificial knee joint operation when the posterior cruciate ligament is removed. The post 511 is not an essential structure of the present disclosure, but may be included in the bearing component 5 depending on a surgical operation.

The groove 512 extends to the lower end of the post 511, and provides a joint surface that is in contact with the femur insertion member (not shown) so as to allow the joint surface to perform joint motion.

Referring to FIG. 9, the lower portion 53 extends downwards through a step at the lower side of the upper portion, and includes a coupling recess 531 and an elastic hook 532 for coupling with the tibial component 3.

The coupling recess 531 is a portion invaginated in the rear surface of the bearing component 5, i.e., at the posterior side P such that during coupling with the tibial component 3 the posterior protrusion 3321 of the tibial component 3 is inserted into the coupling recess 531, thereby forming a firm coupling. Such a coupling relationship is shown in FIG. 10.

The elastic hook 532 protrudes from the front surface of the bearing component, that is, toward the anterior side A. During the coupling with the tibial component 3, the elastic hook 532 is inserted into the anterior recess 3322 of the tibial component 3, thereby forming a firm coupling. Such a coupling relationship is shown in FIG. 10.

The side portion 55 is a portion that connects the upper portion 31 and the lower portion 53, and includes the protrusions 551 that form the periphery of the bearing component 5.

The protrusions 551 are portions protruding downwards from the side portion 55 of the bearing component 5 and have a shape complementary to that of the invagination recesses 3323 in the tibial component 3. As described above, in the process of performing a minimally invasive knee joint replacement operation, the coupling position of the bearing component 5 may be aligned after being inserted into the tibial component 3 in the oblique direction in some cases due to a limitation resulting from the minimization of the skin incision portion. However, according to the present disclosure, the invagination recesses 3323 of the tibial component is capable of guiding coupling at the correct position by receiving the protrusions 551. In addition, since the protrusions 551 in the bearing component 5 and the invagination recesses 3323 in the tibial component 3 are coupled to each other with complementary shapes, the rotation of the bearing component 5 due to the motion of the artificial knee joint can be prevented so that the it is possible to maintain the position of the bearing component 5. Furthermore, since the coupling between the protrusions 551 and the invagination recesses 3323 is made without any gap, it is possible to prevent side effects such as the surrounding tissues being caught in a coupling gap in the recovery process after the operation process is terminated.

Figure 11:
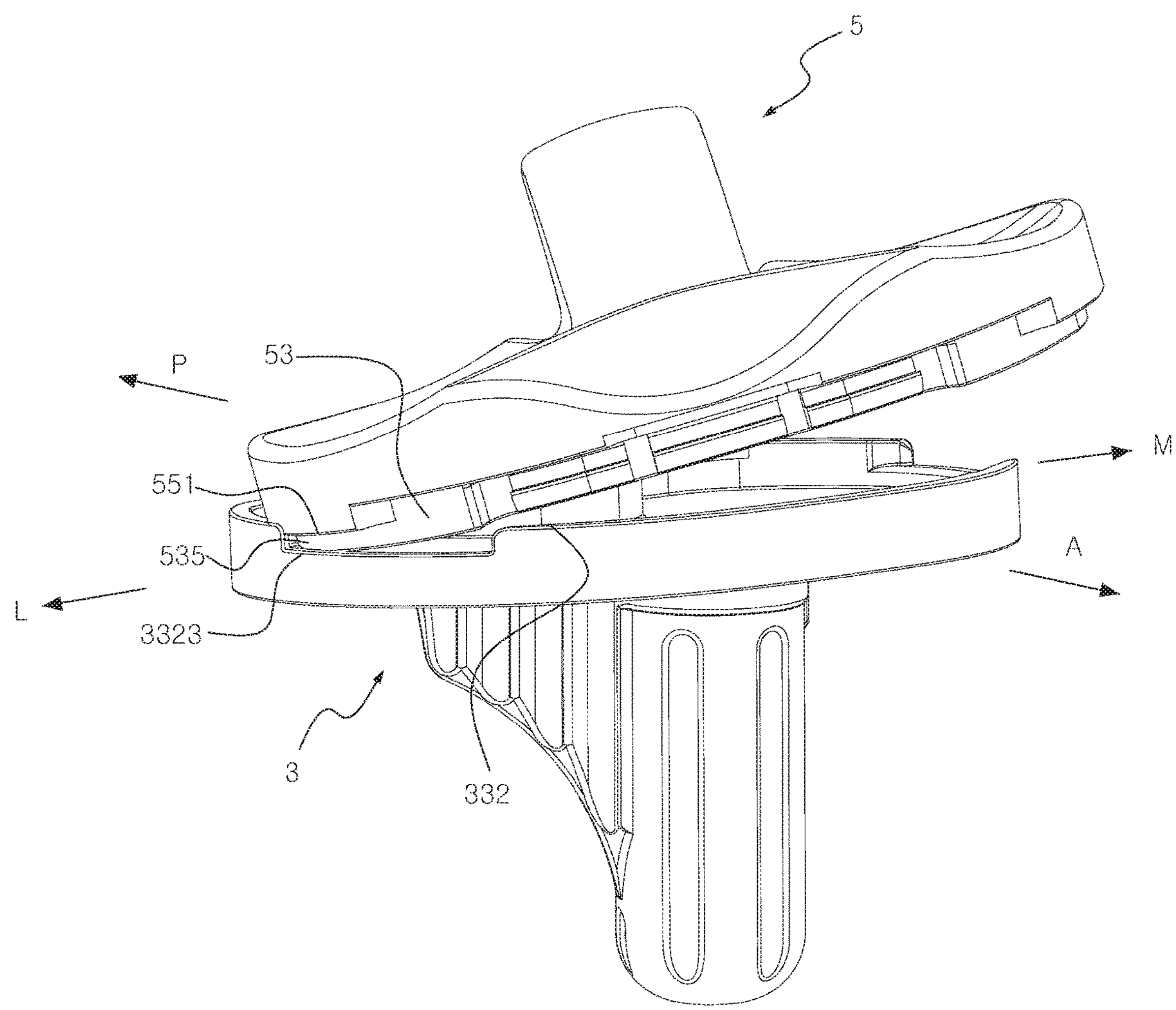
FIG. 11 is a view showing the state of use of the present disclosure, in which interference does not occur when inserting the bearing component into the tibial component in an oblique direction.

FIG. 11 is a view showing the state of use of the present disclosure, in which interference does not occur when inserting the bearing component into the tibial component in an oblique direction.

Figure 12:
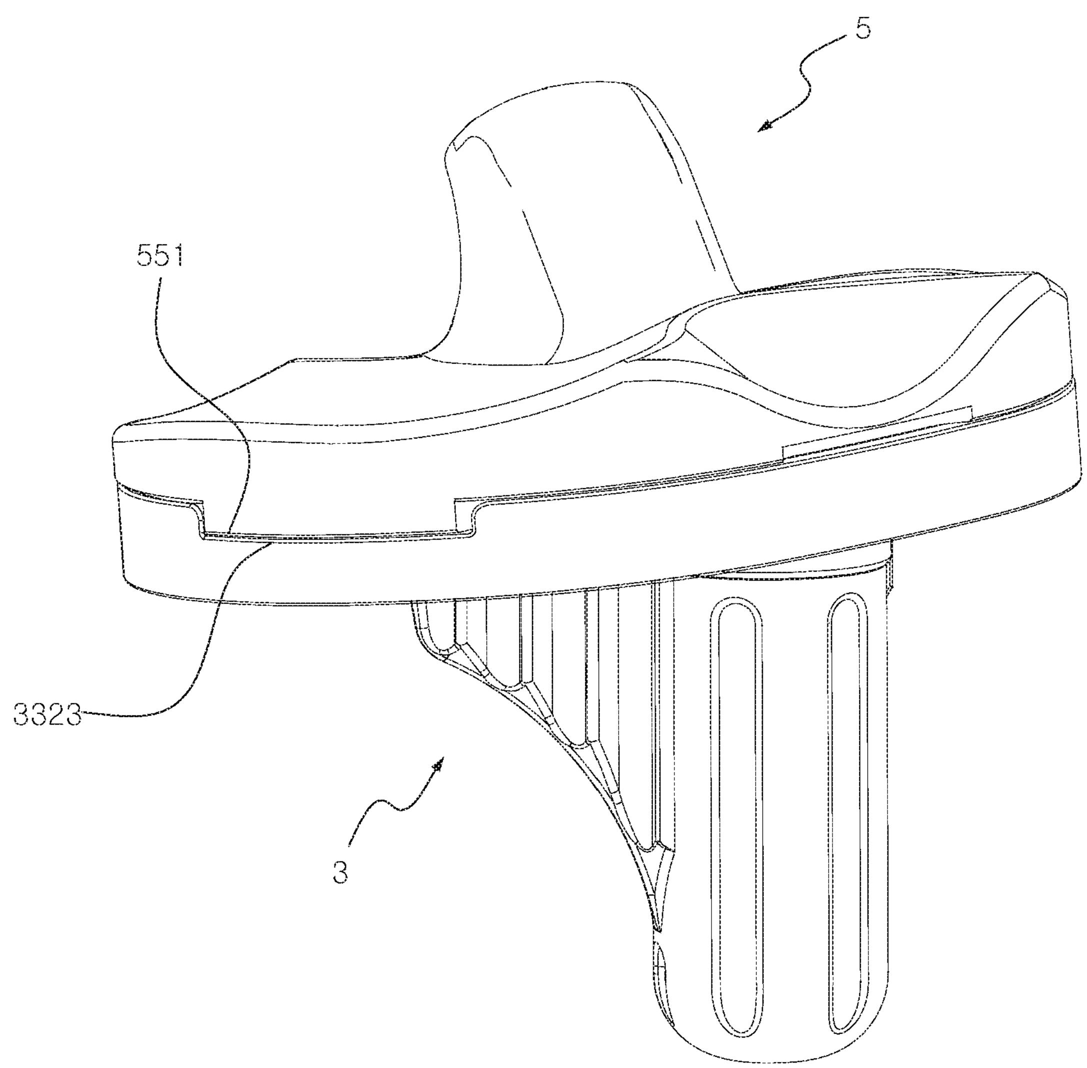
FIG. 12 is a view showing the state in which coupling is made smoothly without causing interference in the process of inserting the bearing component into the tibial component in the oblique direction following the state of FIG. 11.

Referring to FIG. 11, as described above, in the process of surgical operation of minimizing a skin incision portion, the bearing component is inserted in the oblique direction in the state of being tilted from the anterior side A to a space between the posterior side P and the lateral side L due to surrounding tissues. Thereafter, the bearing component 5 is rotated counterclockwise in the oblique state so as to align the coupling portion with the tibial component 3. Unlike the prior art, the present disclosure includes the invagination recesses 3323 in the rim 332 so as to prevent the lower portion 53 of the bearing component from interfering with the rim 332 in the process of aligning the coupling position. As a result, the present disclosure solves the problem of the prior art that causes the lower portion 53 of the bearing component to be aligned in position in the state of overlapping the rim 332 and being floated, whereby the bearing component 5 can be easily coupled with the tibial component 3 at the correct position even if the bearing component 5 is inserted in the oblique direction. The coupling relationship between the protrusions 551 and the invagination recesses 3323 is illustrated in FIG. 12.

The foregoing detailed description illustrates the present disclosure. In addition, the foregoing description is intended to illustrate and explain embodiments of the present disclosure, and the present disclosure may be used in various other combinations, modifications, and environments. That is, it is possible to change or modify the present disclosure within the scope of the concept of the present disclosure disclosed in this specification, within the scope equivalent to the above-described contents, and/or within the scope of the skill or knowledge of a person skilled in the art. The embodiments described above are intended to illustrate the best mode for carrying out the technical idea of the present disclosure, and various modifications required for specific applications and uses of the present disclosure are also possible. Therefore, the detailed description of the present disclosure is not intended to limit the present disclosure to the disclosed embodiments. In addition, the appended claims should be interpreted as covering other embodiments as well.

What is claimed is:

1. An artificial knee joint comprising:

a tibial component configured to be implanted into a proximal end of a tibia, the tibial component comprising:

a base plate including a rim protruding along a peripheral edge; and invagination recesses recessed in the rim across an M-L line of the tibial component on both a lateral side and a medial side; and a bearing component configured to be coupled to the tibial component;

each of the invagination recesses including one end and a remaining end, the one end located at a posterior side of the M-L line and the remaining end located at an anterior side of the M-L line, such that the invagination recesses prevent interference of the tibial component with the bearing component during insertion thereof in an oblique direction with respect to the bearing component.

2. The artificial knee joint of claim 1, wherein the invagination recesses are provided symmetrically with reference to an A-P line.

3. The artificial knee joint of claim 1, wherein the bearing component includes a protrusion configured to be coupled to the invagination recesses, the protrusion extending downward from a periphery of the bearing component corresponding to a position of the invagination recesses formed in the tibial component.

4. The artificial knee joint of claim 3, wherein the protrusion has a shape complementary to a shape of the invagination recesses.

* * * * *